United States Patent [19]

Brunisholz et al.

[11] 4,190,602
[45] Feb. 26, 1980

[54] MONOACETALS OR AROMATIC 1,2-DIKETONES

[75] Inventors: Jean Brünisholz, Monthey; Rudolf Kirchmayr, Münchenstein, both of Switzerland

[73] Assignee: Ciba-Geigy Corporation, Ardsley, N.Y.

[21] Appl. No.: 919,580

[22] Filed: Jun. 22, 1978

Related U.S. Application Data

[62] Division of Ser. No. 701,769, Jul. 2, 1976, abandoned, which is a division of Ser. No. 380,039, Jul. 17, 1973, abandoned.

[30] Foreign Application Priority Data

Jul. 28, 1972 [CH] Switzerland ......................... 11295/72
Jun. 28, 1973 [CH] Switzerland ......................... 9417/73

[51] Int. Cl.$^2$ ............................................. C07C 45/00
[52] U.S. Cl. ................................. 260/590 D; 560/53; 560/255; 204/159.23
[58] Field of Search ............. 260/590 D; 560/53, 255; 204/159.23

[56] References Cited

U.S. PATENT DOCUMENTS

| 3,689,565 | 9/1972 | Hoffmann et al. | 260/590 D |
| 3,728,377 | 4/1973 | Killy et al. | 560/53 |

OTHER PUBLICATIONS

Summerbell et al, J.A.C.S., vol. 81, pp. 633–639, (1959).

Primary Examiner—James H. Reamer
Attorney, Agent, or Firm—Vincent J. Cavalieri

[57] ABSTRACT

Monoacetals of aromatic diketones in which the acetal group is derived from primary mono- or dialkohols are useful as sensitizers in the photochemical polymerization or photochemical crosslinking of polymers. They are prepared from the diketones (benzils) by reaction with sulfites. The sulfites and the benzils may be formed immediately before the reaction in the same vessel without isolating these compounds. Most of the benzil monoacetals are new compounds.

3 Claims, No Drawings

MONOACETALS OR AROMATIC 1,2-DIKETONES

This is a divisional of application Ser. No. 701,769 filed on July 2, 1976, now abandoned which latter application is a divisional of application Ser. No. 380,039, filed on July 17, 1973, now abandoned.

The invention relates to new benzil-monoacetals, to a new process for the production of benzil-monoacetals and to their use as sensitisers for photopolymerisation of polymerisable systems containing unsaturated compounds, as well as to their use for the photochemical cross-linking of polymerisates.

It is known that unsaturated monomers or mixtures thereof with unsaturated polymers can be photochemically polymerised in the presence of suitable sensitisers such as carbonyl compounds containing a halogen in the α-position with respect to the carbonyl group, mercaptans, aromatic disulphides, nitroso compounds, azo compounds, benzoins and benzoin ethers. In industry there is now a demand for sensitisers which, with good storagestability, initiate photopolymerisation more rapidly, and at the same time produce a polymer yield per unit of time higher than that possible with the hitherto known sensitisers. By virtue of the employment of such improved sensitisers, the expensive industrial UV-irradiation equipment could be utilised more economically.

Compounds as defined below have now been found that are suitable, in a surprisingly advantageous manner, as sensitisers for photopolymerisation of polymerisable systems containing unsaturated compounds. The advantages they offer are, in particular, a more rapid start of photopolymerisation and the higher time-yield attainable in consequence, with, at the same time, excellent dark-storage stability. Moreover the compounds are suitable as sensitisers for the photochemical crosslinking of linear polymerisates, such as, e.g. polyethylene.

The compounds usable according to the invention correspond to formula I or Ia:

$$Ar^1-C=O \quad (I) \qquad Ar^1-C=O \quad (Ia)$$
$$| \qquad\qquad\qquad\qquad |\diagup O \diagdown$$
$$Ar^2-C(OCH_2R^1)_2 \qquad Ar^2-C \qquad R^2$$
$$\qquad\qquad\qquad\qquad\qquad \diagdown O \diagup$$

wherein $R^1$ represents hydrogen, alkyl having 1 to 5 carbon atoms, alkenyl having 2 or 3 carbon atoms, aralkyl having 7 to 9 carbon atoms, aralkenyl having 8 or 9 carbon atoms, or a group $-(CH_2)_n-X$, X represents halogen, $-OR^3$, $-SR^3$, $-OAr^3$, $$\qquad\qquad O \qquad\quad O$$
$$\qquad\qquad \|\qquad\quad \|$$
$$-O-C-R^3 \text{ or } -C-OR^3,$$

n represents a whole number from 1 to 3

$R^2$ represents a group $$\qquad R^4 \qquad\qquad R^4$$
$$\qquad | \qquad\qquad |$$
$$-CH_2-CH- \text{ or } -CH_2-CH-CH_2-,$$

$R^3$ represents alkyl having 1 to 4 carbon atoms,
$R^4$ represents hydrogen or alkyl having 1 to 18 carbon atoms, and
$Ar^1$, $Ar^2$ and $Ar^3$ each independently represent a phenyl radical unsubstituted or at most trisubstituted by halogen, alkyl or —Oalkyl having 1 to 4 carbon atoms or by phenyl.

Compounds of formula I or Ia which are preferably used are such compounds wherein $R^1$ represents hydrogen, alkyl having 1 to 3 carbon atoms, benzyl, β-styrene or a group $-(CH_2)_n-X$, X represents chlorine, bromine, $-OR^3$, $-SR^3$, $-OAr^3$ or $-SAr^3$, n represents 1 or 2,
$R^2$ represents $-(CH_2)_3-$ or $-(CH_2)_2-$,
$R^3$ represents alkyl having 1 to 3 carbon atoms,
$Ar^1$ and $Ar^2$ each independently represent a phenyl radical unsubstituted or mono- or disubstituted by chlorine, bromine, alkyl or -Oalkyl having 1 to 3 carbon atoms, and
$Ar^3$ represents phenyl.

Particularly preferred is the use of compounds of formula I wherein $R^1$ represents hydrogen, alkyl having 1 to 3 carbon atoms or a group $-CH_2-X$, X represents chlorine, bromine or $-OCH_3$ and
$Ar^1$ and $Ar^2$ represent phenyl.

With the exception of the dimethylacetal and monoethyleneacetal of benzil, these monoacetals of aromatic 1,2-diketones of formula I or Ia are new compounds. The invention concerns therefore also new compounds of formula I or Ia wherein $R^1$ represents alkyl having 1 to 5 carbon atoms, alkenyl having 2 or 3 carbon atoms, aralkyl having 7 to 9 carbon atoms, aralkenyl having 8 or 9 carbon atoms or a group $-(CH_2)_n-X$, X represents halogen, $-OR^3$, $-SR^3$, $-OAr^3$, $-SAr^3$, $$\qquad\qquad O \qquad\quad O$$
$$\qquad\qquad \|\qquad\quad \|$$
$$-O-C-R^3 \text{ or } -C-OR^3,$$

n represents a whole number from 1 to 3,
$R^2$ represents a group $$\qquad R^4 \qquad\qquad R^4$$
$$\qquad | \qquad\qquad |$$
$$-CH_2-CH-, \quad -CH_2-CH-CH_2-$$

or $-(CH_2)_3-$,
$R^3$ represents alkyl having 1 to 4 carbon atoms,
$R^4$ represents alkyl having 1 to 18 carbon atoms, and
$Ar^1$, $Ar^2$ and $Ar^3$ each independently represent a phenyl radical unsubstituted, or at most trisubstituted by halogen, alkyl or -Oalkyl having 1 to 4 carbon atoms or phenyl, or, if $Ar^1$ or $Ar^2$ or $Ar^1$ and $Ar^2$ represent a phenyl radical substituted as defined, $R^1$ and $R^4$ can also represent halogen.

Preferred compounds of formula I or Ia are compounds wherein $R^1$ represents alkyl having 1 to 3 carbon atoms, vinyl, benzyl, β-styrene or a group $-(CH_2)_n-X$, X represents chlorine, bromine, $-OR^3$, $-SR^3$, $-OAr^3$ or $SAr^3$, n represents 1 or 2,
$R^2$ represents $-(CH_2)_3-$,
$R^3$ represents alkyl having 1 to 3 carbon atoms,
$Ar^1$ and $Ar^2$ each independently represent a phenyl radical unsubstituted, or mono- or disubstituted by chlorine, bromine, alkyl or -Oalkyl having 1 to 3 carbon atoms, and Ar$^3$ represents phenyl;

or, if Ar$^1$ or Ar$^2$ or Ar$^1$ and Ar$^2$ represent a phenyl radical substituted as defined, R$^1$ can also represent hydrogen and R$^2$ also —CH$_2$-CH$_2$—;

particularly preferred compounds, however, are such wherein

R$^1$ represents alkyl having 1 to 3 carbon atoms or a group —CH$_2$—X,

X represents chlorine, bromine or —OCH$_3$ and

Ar$^1$ and Ar$^2$ represent phenyl.

Where R$^1$, R$^3$ and R$^4$ of formula I denote alkyl radicals, then, within the given limits, these can be, for example, methyl, ethyl, propyl, isopropyl, butyl, sec.butyl, tert.butyl, amyl, hexyl, octyl, dodecyl, 2-ethylhexyl or octadecyl. R$^1$ can be an alkenyl radical such as vinyl, α-methylvinyl, propenyl or allyl. As aralkyl or aralkenyl, R$^1$ can be, e.g. benzyl, α-methylbenzyl, α,α-dimethylbenzyl, β-phenylethyl or β-phenylvinyl.

Examples for Ar$^1$, Ar$^2$ and Ar$^3$ as a substituted phenyl radical are: 4-chlorophenyl, 2-bromophenyl, 2,4-dichlorophenyl, 3-methylphenyl, 4-sec.butylphenyl, 2-chloro-4-ethylphenyl, 4-ethoxyphenyl, 2-methoxy-4-chlorophenyl, 2,4,6-trichlorophenyl or 3,5-dichloro-4-propoxyphenyl.

Examples of compounds of formula I are: benzil-diethylacetal, benzil-dipropylacetal, benzil-dibutylacetal, benzil-di(β-phenylethyl)acetal, benzil-diallylacetal, benzil-di(γ-phenylallyl)acetal, benzil-di(2-methoxyethyl)acetal, benzil-di(2-ethoxyethyl)acetal, benzil-di(2-chloroethyl)acetal, benzil-di(2-bromoethyl)acetal, benzil-di(2-chloropropyl)acetal, benzil-di(2-methylthioethyl)acetal, benzil-di(2-tert.butylthioethyl)acetal, benzil-di(2-phenylthioethyl)acetal, benzil-di(2-phenoxyethyl)acetal, benzil-di(2-acetoxyethyl)acetal, benzil-di(2-butyroxyethyl)acetal, benzil-di(2-ethoxycarbonylethyl)acetal, benzil-di(3-methoxycarbonylpropyl)acetal, 4,4'-dimethylbenzil-dimethylacetal, 4,4'-diphenylbenzil-diethylacetal, 2,2'-dimethoxybenzil-dipropylacetal, 4,4'-dichlorobenzil-dimethylacetal, 4,4'-dibromobenzil-dimethylacetal, 4,4'-diisopropylbenzil-di(2-chloroethyl)acetal, 2,4,2',4'-tetramethylbenzil-diethylacetal, 4-chlorobenzil-dimethylacetal, 4-ethoxybenzil-diethylacetal, 4-phenylbenzil-dimethylacetal, 2,4,6-trimethylbenzil-di(2-methoxyethyl)acetal.

Examples of compounds of formula Ia are: 2-phenyl-2-benzoyl-4-methyl-1,3-dioxolane, 2-phenyl-2-benzoyl-4-hexyl-1,3-dioxolane, 2-phenyl-2-benzoyl-1,3-dioxane, 2-phenyl-2-benzoyl-5-ethyl-1,3-dioxane, 2-(4-chlorophenyl)-2-(4-chlorobenzoyl)-1,3-dioxolane, and 2-(4-tolyl)-2-(4-methylbenzoyl)-1,3-dioxane.

The cyclic monoacetals of aromatic 1,2-diketones of formula Ia can be produced by acetalisation of the corresponding benzoins, and subsequent oxidation of the benzoinacetal to benzil-monoacetal, a process described in the case of monoethyleneacetal of benzil in the Journal of Amer. Chem. Soc., 81, 633 (1959), and represented below in terms of the following formulae:

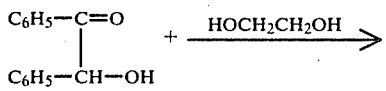

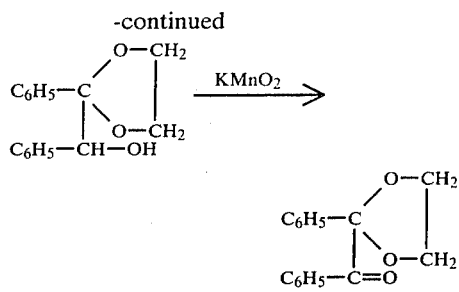

This process is applicable also for other benzil-monoacetals of formula Ia.

No generally applicable processes for the production of non-cyclic monoacetals of aromatic 1,2-diketones of formula I have hitherto been known. The dimethylacetal of benzil was produced by reaction of benzil with a large excess of barium oxide and methyliodide in dimethylformamide (Chem. Berichte 94, 2258 (1961)). After separation of the benzilic acid methyl ester, occurring as by-product, in several purifying operations, benzil-dimethylacetal is obtained in 40% yield. This process is too uneconomical for commercial production, since it requires expensive reagents and produces low yields. Nor is it commercially applicable for the production, not described, of the higher homologues.

A process has now been found which enables monoacetals of aromatic 1,2-diketones of formula I to be produced, in a generally applicable manner, simply and in high yield and degree of purity. This process comprises the reaction of an aromatic 1,2-diketone either with a sulphurous acid ester in the presence of an anhydrous acid and of an alcohol, or with thionyl chloride and an alcohol.

There is preferably used for this purpose an aromatic 1,2-diketone of formula II

wherein Ar$^1$ and Ar$^2$ each independently represent a phenyl radical which is unsubstituted or at most trisubstituted by halogen, alkyl or alkoxy having 1 to 4 carbon atoms or by phenyl, and this reacted with a sulphurous acid ester of the formula (R$^1$CH$_2$O)$_2$SO in the presence of an anhydrous acid and of an alcohol of the formula R$^1$CH$_2$OH, or with thionyl chloride and an alcohol of the formula R$^1$CH$_2$OH, whereby R$^1$ represents hydrogen, alkyl having 1 to 5 carbon atoms, alkenyl having 2 or 3 carbon atoms, aralkyl having 7 to 9 carbon atoms, aralkenyl having 8 or 9 carbon atoms or a group —(CH$_2$)$_n$—X wherein n denotes a whole number of 1 to 3, and X represents halogen, —OR$^3$, —SR$^3$, —OAr$^3$, SAr$^3$,

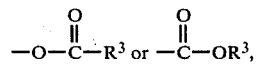

and R$^3$ an alkyl group having 1 to 4 carbon atoms and Ar$^3$ a phenyl radical which is unsubstituted or at most trisubstituted by halogen, alkyl or alkoxy having 1 to 4 carbon atoms, or by phenyl.

Examples of aromatic 1,2-diketones which can be used for this process are benzil and substituted benzils such as, e.g. 4,4'-dimethylbenzil, 4,4'-diisopropylbenzil, 4,4'-diphenylbenzil, 2,2'-dimethoxybenzil, 4-methylbenzil, 3-methoxybenzil, 2,2'-dimethylbenzil, 4-chloro-4'-phenylbenzyl, 4,4'-dichlorobenzil, 3,3'-dibromobenzil, 2,4,2',4'-tetramethylbenzil, 2,4,6-trimethylbenzil, 2,4-dichloro-4'-methylbenzil. The production of these benzil derivatives is described in the literature; they are produced, for example, by oxidation of the corresponding benzoins.

Examples of sulphurous acid esters which can be used for this process are dimethylsulphite, diethylsulphite, dipropylsulphite, dibutylsulphite, dihexylsulphite, diallylsulphite, di(β-phenylethyl)sulphite, di(γ-phenylallyl)sulphite, di(2-chloroethyl)sulphite, di(2-methoxyethyl)sulphite, di(2-phenoxyethyl)sulphite, di(2-methylthioethyl)sulphite, di(2-phenylthioethyl)sulphite, di(2-acetoxyethyl)sulphite or di(3-carbomethoxypropyl)sulphite. These sulphites are produced by processes known from the literature, e.g. by reaction of the corresponding alcohols with thionyl chloride.

The anhydrous acid employed for the purpose of accelerating the formation of acetal can be an anhydrous mineral acid such as, e.g. sulphuric acid or hydrochloric acid, or a Lewis acid such as, e.g. borofluoride or its complexes. It is preferable to use concentrated sulphuric acid, and in an amount of at least one mole per mole of diketone.

The alcohol employed is advantageously the alcohol corresponding to the sulphurous acid ester, that is, for example, methanol with application of dimethylsulphite, or isopropanal with application of diisopropylsulphite. If the diketones are reacted with thionyl chloride and a primary monoalcohol, then as such there can be used, e.g. methanol, ethanol, propanol, butanol, hexanol, allyl alcohol, β-phenylethyl alcohol, γ-phenylallyl alcohol, 2-chloroethanol, 2-methoxyethanol, 2-phenoxyethanol, 2-methylthioethanol, 2-phenylthioethanol, 2-acetoxyethanol, hydracrylic acid methyl ester or glycolic acid butyl ester.

The reaction of the diketones with sulphurous acid esters in the presence of an acid and of an alcohol is generally performed at a temperature of 20° to 120° C., preferably at 40° to 100° C.

The reaction of the diketones with a mixture of thionyl chloride and alcohol is advantageously performed with cooling to ca. 02 to 20° C., whereby the sulphite forms. The subsequent reaction is, as described above, carried out at elevated temperature.

A modification of the process consists in reacting a benzoin firstly with sulphuryl chloride and subsequently with thionyl chloride and an alcohol. Preferably used in this case is a benzoin of formula III

which is reacted with sulphuryl chloride and then with thionyl chloride and an alcohol, R¹CH₂OH, whereby Ar¹, Ar² and R¹ have the above defined meanings.

Examples of such benzoins are, besides the unsubstituted benzoin, symmetrically or unsymmetrically substituted benzoins such as, e.g. 4-methylbenzoin, 4,4'-dimethylbenzoin, 2,2'-dimethylbenzoin, 4,4-diisopropylbenzoin, 4,4'-diphenylbenzoin, 3-methoxybenzoin, 2,2'-dimethoxybenzoin, 4,4'-dichlorobenzoin, 4-chloro-4'-phenylbenzoin, 3,3'-dibromobenzoin, 2,4,2',4'-tetramethylbenzoin, 2,4,6-trimethylbenzoin or 2,4-dichloro-4'-methylbenzoin. The production of these benzoins is described in the literature; in particular, they can be produced by condensation of the corresponding aromatic aldehydes.

In the case of this process variant, there is formed from the benzoin employed, by an oxidation reaction with the sulphuryl chloride, the corresponding benzil which, without being isolated, is converted by reaction with thionyl chloride and an alcohol into benzil-monoacetal.

The procedure used is to suspend the benzoin in the sulphuryl chloride and to heat the suspension slowly to about 25°–50° C. After completion of oxidation, the excess sulphuryl chloride is distilled off and, after cooling to room temperature, the reaction with thionyl chloride and the alcohol performed as described above.

The isolation of benzil-monoacetals from the reaction mixtures is effected by known processes: e.g. by concentration by evaporation of the solution, by the addition of water or by cooling. Yields of over 80% of crude monoacetal are obtained; as required, the resulting product can be purified by recrystallisation or distillation or by other known methods.

The physical properties of the benzil-monoacetals are dependent to a great extent on the nature and position of the substituents; in general, the products are low-melting or oily compounds, which at room temperature are stable to an unlimited extent.

The benzil-monoacetals producible according to the invention can be used as sensitisers for photopolymerisation of polymerisable systems containing unsaturated compounds. Such systems are, for example, unsaturated monomers such as acrylic acid methyl ester, -ethyl ester, -n- or tert. butyl ester, methacrylic acid alkyl esters such as methylmethacrylate or ethylmethacrylate, di-(meth)-acrylates of aliphatic diols, acrylonitrile, methacrylonitrile, acrylamide, methacrylamide, N,N-disubstituted acrylamides and methacrylamides, vinylacetate, vinylacrylate, vinylpropionate, succinic acid divinyl ester, isobutylvinyl ether, butanediol-1,4-divinyl ether, styrene, alkylstyrene, halostyrenes, divinylbenzenes, vinylnaphthalene, N-vinylpyrrolidone, vinyl chloride, vinylidene chloride, diallylphthalate, diallylmaleate, triallylisocyanurate, triallylphosphate, ethylene glycol diallyl ether, pentaerythritol-tetraallyl ether, and mixtures of such monomers.

Photopolymerisable systems are, in addition, unsaturated polymers and mixtures thereof with unsaturated monomers. These include, in particular, the mixtures of unsaturated polyesters with unsaturated monomers. By unsaturated polyesters are meant, for example, polycondensation products from α,β-unsaturated dicarboxylic acids or their derivatives with polyols. Examples of α,β-unsaturated dicarboxylic acids or their derivatives are maleic acid, maleic acid anhydride, fumaric acid, mesaconic acid, and citraconic acid. Besides the unsaturated dicarboxylic acids, it is also possible to incorporate, for the purpose of adjustment of the degree of unsaturation, saturated dicarboxylic acids or dicarboxylic acids inert to polymerisation. Examples in this case are succinic acid, sebacic acid, isophthalic acid, phthalic acid, halogenated phthalic acids or 3,6-endomethylene-Δ⁴-tetrahydrophthalic acid, as well as the anhydrides of these dicarboxylic acids.

The polyols employed for the production of polycondensation products are mainly glycols such as ethylene glycol, propanediol-1,2-diethylene glycol, 1,3-propylene glycol, 1,4-tetramethylene glycol as well as triethylene glycol.

Further modifications of unsaturated polyester resins are possible by incorporation of monocarboxylic acids or monoalcohols.

These unsaturated polyesters are usually employed in admixture with unsaturated monomers containing allyl or vinyl groups, preferably with styrene. After the addition of benzil-monoacetals of formula I or Ia, such mixtures can be photopolymerised in an advantageous manner to thus obtain moulding and coating compounds.

Moulding compounds which can be photopolymerised with compounds of formula I or Ia are, for example, so-called air-drying moulding compounds. These are unsaturated polyesters containing, besides $\alpha,\beta$-unsaturated dicarboxylic acid esters, also $\beta,\gamma$-unsaturated ether radicals.

Coating compounds that can be photopolymerised with compounds of formula I or Ia are, for example, lacquer coatings from unsaturated monomers and unsaturated polymers. These lacquers may also be photopolymerised by the so-called active-base process (Aktivgrundverfahren). The coating compound is in this case applied with the photo-initiator to a peroxide-containing layer previously applied to the substrate, and subsequently photopolymerised.

The photopolymerisable compounds or mixtures can be stabilised by addition of the usual thermal inhibitors which are employed in the production of light-sensitive compounds. As examples of these, mention may be made of hydroquinone, p-quinone, p-methoxyphenol, $\beta$-naphthylamine, $\beta$-naphthol and phenols. For enhancement of the dark-storage stability, additions can moreover be made of copper compounds such as copper naphthenate, -stearate or -octoate, phosphorus compounds such as triphenylphosphine, tributylphosphine, triethylphosphite, triphenylphosphite or tribenzylphosphate, quaternary ammonium compounds such as tetramethylammonium chloride or trimethylbenzylammonium chloride or hydroxylamine derivatives such as N,N-diethylhydroxylamine. Furthermore, the photopolymerisable compounds or mixtures can contain chain-transfer agents such as triethanolamine or cyclohexene.

In order to exclude the inhibiting action of atmospheric oxygen, it is advantageous to make additions of paraffins, waxes or wax-like substances to the coating compounds with the photosensitisers. These added substances float out at the commencement of photopolymerisation and thus prevent the inhibiting action of the atmospheric oxygen.

A further possibility of preventing the inhibiting action of the atmospheric oxygen is for the process to be performed under inert gas, or for fillers permeable to UV-light, such as, e.g. certain silicates, to be added to the polyester resin. The formulations filled in this way cure, even in air, rapidly under UV-irradiation, because the content of bonding agent is reduced at the surface.

Also the introduction of autoxidisable groups into the resin to be cured can eliminate the inhibiting action of the atmospheric oxygen. For example, this can be effected by copolymerisation with certain allyl compounds Furthermore, small amounts of conventional UV-absorbers can be added to the moulding and coating compounds, without the reactivity of the photosensitisers being appreciably impaired. The coating and moulding compounds may also contain slight amounts of the usual carriers and fillers, as well as so-called thixotropic agents, such as glass fibres, synthetic fibres, silicic acid and talcum.

A further application of compounds of formula I is the photochemical cross-linking of polymerisates, specially of olefin polymerisates. By olefin polymerisates are meant in this connection polyolefins such as high- and low-pressure polyethylene polypropylene, polybutylene, polyisobutylene and ethylene-vinylacetate-copolymerisates. In addition, copolymerisates from olefins such as ethylene, propylene, butylene or isobutylene can be cross-linked by UV-irradiation with the aid of the benzil-monoacetals.

Benzil-monoacetals are moreover applicable for the production of photopolymerised elements from which, after irradiation and by washing-out, relief profiles for printing purposes can be produced. Suitable as unsaturated polymers in photopolymerisable layers for the production of relief profiles for printing purposes are, in particular, linear synthetic polyamides. Photopolymerisable unsaturated monomers, which are used in the mentioned polymers in light-sensitive layers for the production of relief profiles, are preferably those which contain at least two polymerisable olefinic double bonds and, besides the double bonds, also amide groups such as, e.g. methylene-bis-acrylamide, methylene-bis-methacrylamide as well as bis-acryl- or bis-methacrylamides of diamines.

A further application of the benzil-monoacetals as photosensitisers is in the drying, by UV-irradiatin, of printing pastes containing as bonding agents unsaturated monomers and unsaturated polymers. Based on bonding agents having, for example, conjugated double bonds, printing pastes which dry in a short time under the action of UV-rays can be produced.

Examples of such bonding agents are natural or synthetic conjuen oils, unsaturated polyester resins or polyfunctional acrylates or methacrylates. Such printing-paste bonding agents frequently contain as additives chain-transfer agents such as triethanolamine or cyclohexene, anti-inhibiting agents such as diallylphthalate-prepolymers, or stabilisers such as diethylhydroxylamine. For such printing-paste bonding agents, the benzil-monoacetals according to the invention are particularly well-suited catalysts for photochemical curing.

The benzil-monoacetals of formula I or Ia are used for the mentioned fields of application advantageously in amounts of 0.1 to 20 per cent by weight, preferably in amounts of ca. 0.5 to about 5 per cent by weight, and either singly or in admixture with each other.

The addition of the sensitisers to the photopolymerisable systems is generally effected by a simple stirring-in, since most of these systems are liquid. Usually there is obtained a solution of the sensitisers according to the invention, in consequence of which their homogeneous distribution and the transparency of the polymerisates are ensured.

Polymerisation of the systems sensitised in such a manner is performed, using known methods of photopolymerisation, by irradiation with light rich in short-wave radiation. Suitable light sources for the irradiation of the substrates containing the photosensitisers of formula I or Ia are medium-pressure, high-pressure and low-pressure mercury vapour lamps, as well as superactinic fluorescent lamps, of which the emission maxima is in the range of between 300 and 400 m$\mu$.

The production and use according to the invention of the said benzil-monoacetals are further illustrated in the following examples. The term 'parts' denotes parts by weight and temperatures and expressed in degrees Centigrade.

EXAMPLE 1

Production of benzildimethylacetal (a) Method A 210.0 g of benzil and 440 g of dimethylsulphite are dissolved at reflux temperature in 1000 ml of anhydrous methanol. An addition is then made dropwise to this solution at 60°–65° in the course of 4 hours, with stirring, of 200.0 g of concentrated sulphuric acid. This reaction mixture is subsequent refluxed for a further 4 hours. After this length of time, a sample examined by thin-layer chromatography (neutral silica gel; solvent: toluene/ligroin 9:1) shows only traces of benzil. The slightly yellow solution is cooled and then neutralised with potassium carbonate. The precipitated potassium sulphate is removed and an amount of 2 ml of trimethylphosphite then added to the filtrate to effect separation of the residual traces of benzil; the temperature is maintained for 2 hours at room temperature, the filtrate then concentrated by evaporation to dryness and the residue distilled in vacuo. Benzildimethylacetal distills at 140°–141°/0.5 mm in the form of a colourless oil, which crystallises in the receiver; M.P. 62°–63°. Benzildimethylacetal is obtained by this process in a yield of 85–90% of theory, calculated on the amount of benzil used. The absorption of the carbonyl bands of the benzildimethylacetal obtained lies in the IR-spectrum at 5.91$\mu$; $\lambda_{max.}$=250.5 nm.

(b) Method B

An amount of 210.2 g of benzil is suspended in 238.0 g of thionyl chloride. This suspension is cooled to 4° and, with slow stirring, 128.0 g of methanol added dropwise in the course of 2 hours, whereby the temperature is maintained between 2° and 7°. After completion of the addition, the reaction mixture is allowed to slowly warm up to room temperature to obtain a clear yellow solution. This is thereupon heated within 30 minutes to 50° and stirred for 1 hour at this temperature. The excess dimethylsulphite is distilled off in vacuo, the oily residue then taken up in 400 ml of isopropanol, and 25 g of potassium carbonate and 7 ml of trimethylphosphite are added to the clear solution. A crystalline precipitate forms as the solution cools. An addition is made dropwise at between 7° and 10° of 350 ml of water, and the reaction mixture stirred. The crystalline precipitate is filtered off under suction, washed with isopropanol/water 1:1 and dried at 40° in vacuo.

Benzildimethylacetal is obtained by this process in the form of white crystals in a yield of 84% of theory.

(c) Method C

An amount of 106.0 g of benzoin is suspended in 135 g of sulphuryl chloride and this suspension stirred for 12 hours at room temperature. Excess sulphuryl chloride is then distilled off and the residue suspended in 120 g of thionyl chloride. An addition is made dropwise to this suspension at between 2° and 7°, in the course of 2 hours, of 65 g of methanol. After the addition, the reaction mixture is allowed to slowly come up to room temperature, whereby a clear yellow-brown solution is obtained. This is heated within 30 minutes to 50° and stirred for 1 hour at this temperature. The excess dimethylsulphite is distilled off in vacuo and the oily residue taken up in 200 ml of isopropanol. A clear solution is obtained, to which are added 15 g of potassium carbonate and 5 ml of trimethylphosphite. A crystalline precipitate is formed on cooling. A further addition is made of 200 ml of water and the crystal mass then filtered off under suction; it is washed with isopropanol/water 1:1 and dried at 40° in vacuo.

By this method, benzildimethylacetal is obtained in the form of white crystals in a yield of 79% of theory.

EXAMPLES 2–4

Production of benzil-dialkylacetals

An amount of 21 g of benzil is suspended in 23.8 g of thionyl chloride. The suspension is cooled to ca. 5° and alkanol slowly added dropwise in the amount given in column 2 of the following table. Cooling is removed and stirring carried out for 4 hours at room temperature and for a further 1 hour at 50°. The yellow solution is concentrated in vacuo, the oily residue dissolved in 40 ml of isopropanol, and 3 g of potassium carbonate and 0.6 ml of trimethylphosphite then added to the solution. After the addition of 30 ml of water, a crystalline precipitate of the product listed in column 3 of the table is formed, which is filtered off and recrystallised from isopropanol.

| Example | Alcohol employed | Product | Melt. point Boil. point |
|---|---|---|---|
| 2 | 19 g of ethanol | benzene-diethylacetal | M.P. 61–62° |
| 3 | 24 g of n-propanol | benzene-di-n-propyl-acetal | M.P. 46–47° |
| 4 | 30 g of n-butanol | benzene-di-n-butyl-acetal | B.P.$_{0.5}$ 175° |

EXAMPLE 5

Production of benzil-di-$\beta$-methoxyethyl-acetal (a) Method B

An amount of 21.0 g of benzil is suspended in 23.8 g of thionyl chloride and the suspension cooled to 0°. An addition is made dropwise to this suspension, within 30 minutes, of 30.4 g of $\beta$-methoxyethanol, whereby the temperature is maintained at between 2° and 7° by cooling. The reaction mixture is raised within 6 hours to room temperature to obtain a clear solution. This is heated for 1 hour at 60°. The clear solution is concentrated in a rotary evaporator; the residue is then taken up in 40 ml of isopropanol, and 3 g of potassium carbonate and 0.6 ml of trimethylphosphite are added. Cooling is applied as 35 ml of water is added dropwise, and white crystals commence to precipitate. These are filtered off under suction and recrystallised from ethanol. Benzene-di-$\beta$-mehoxyethyl-acetal is obtained by this means in the form of white crystals having a melting point of 67°–69°.

(b) Method C

An amount of 21.2 g of benzoin is placed into 27.0 g of sulphuryl chloride. This mixture is stirred for 6 hours at room temperature, whereby the reaction mixture gradually turns yellow as an intense evolution of gas occurs. When all the benzoin has oxidised to benzil, the excess sulphuryl chloride is distilled off in vacuo, and the residue taken up in 23.8 g of thionyl chloride. An addition is then made dropwise at 5° of 30.4 g of ethylene glycol monomethyl ether, and the process continued as described in Example 1. Benzil-di-$\beta$-methoxyethylacetal is obtained in the form of white crystals having a melting point of 67°–69°.

EXAMPLE 6

Production of benzil-di-β-chloroethyl-acetal

A suspension of 21.0 g of benzil in 23.8 g of thionyl-chloride is cooled to 0°, and 35.3 g of 2-chloroethanol added dropwise to the suspension at between 0° and 5° in the course of 30 minutes. The reaction mixture is stirred for 6 hours at room temperature and subsequently for 1 hour at 50°–60°; it is then concentrated in a rotary evaporator, and 3 g of potassium carbonate and 0.6 ml of trimethylphosphite are added to the residue; the whole is afterwards taken up in 40 ml of isopropanol. Water is added and a crystalline precipitate formed. This is filtered off under suction and recrystallised from isopropanol to obtain benzil-di-β-chloroethyl-acetal in the form of white crystals, M.P. 58°–59°.

EXAMPLE 7

Production of benzil-di-β-bromoethyl-acetate 50.0 g of 2-bromoethanol is added dropwise, with cooling and in the course of 30 minutes, to a suspension, cooled to 0°, of 21.0 g of benzil in 23.8 g of thionyl chloride. After completion of the addition, the reaction mixture is stirred for 8 hours at room temperature and then for 1 hour at 50°–60°. It is afterwards concentrated in vacuo, the residue dissolved in 40 ml of isopropanol, and 3.0 g of potassium carbonate and 0.6 ml of trimethylphosphite added to the solution. Water is added to obtain a crystalline precipitate, which is filtered off under suction and recrystallised from isopropanol. The resulting product is benzil-di-β-bromoethyl-acetal in the form of white crystals having a melting point of 79°–80°.

EXAMPLE 8

Photopolymerisation of methylacrylate

An amount of 0.1 g in each case of various known sensitisers and of sensitisers according to the invention is dissolved in 10.0 g of freshly distilled acrylic acid methyl ester. This solution contained in a quartz glass tube of 1.5 cm diameter is irradiated, in a thermostatically controlled water bath at 25°, with a high-pressure mercury-vapour lamp. The lamp is situated at a distance of 10 cm from the quartz tube. Nitrogen is passed for 1 minute before irradiation through the solution of the respective sensitisers, and the flow of nitrogen is maintained during irradiation. The polymerisation of the monomers occurring during exposure to the light is indicated by a rise in temperature of the irradiated solution. The exposure time is 20 seconds. Immediately after irradiation, the irradiated solution is cooled in order to prevent a thermal polymerisation. The solution of the formed polymerisate in the monomer is rinsed with small amounts of ethylacetate in a round flask, and the solvent and the unpolymerised monomeric fraction are subsequently distilled off in a rotary evaporator. The polymeric residue is dried in a vacuum drying chamber at 50°–60° and afterwards weighed.

The amounts of polyacrylic acid methyl ester obtained with various sensitisers by the above test procedure are shown in the following table.

Table 1

| Per cent by weight | Sensitiser | Start time in seconds | Amount of formed polyacrylic acid methyl ester in per cent by weight |
|---|---|---|---|
| 1 | benzoin | 11 | 6.2 |
| 1 | benzoinisopropyl ether | 8 | 7.7 |
| 1 | benzil-dimethyl-acetal | 4 | 16.1 |

Without the photo-initiator, the amount of polymerisation is below 0.1%.

From the values shown in Table 1, it is clear that, compared with known photo-initiators, the photosensitisers according to the invention initiate polymerisation more rapidly and give higher polymer yields.

EXAMPLE 9

Photopolymerisation of methylacrylate

With the same test procedure as described in Example 8, solutions of known photosensitisers and photosensitisers according to the invention are irradiated in acrylic acid methyl ester. After various exposure times, an aliquotic specimen of the irradiated solution is concentrated by evaporation, and the polymeric residue dried and weighed. The results of this test series are given in the following Table 2.

Table 2

| Per cent by weight | Sensitiser | Amount of formed polyacrylic acid methyl ester in per cent by weight after an irradiation time of: | | |
|---|---|---|---|---|
| | | 10 seconds | 29 seconds | 30 seconds |
| 1 | benzoin | — | 6.2 | 11.8 |
| 1 | benzoinisopropyl ether | 4.2 | 7.7 | 13.4 |
| 1 | benzildimethyl-acetal | 8.0 | 16.1 | 26.7 |

From the values listed in Table 2, it is clearly shown that, compared with known photo-initiators, the photosensitisers according to the invention initiate polymerisation more rapidly and give higher polymer yields.

EXAMPLE 10

Curing of polyester resin

An amount of 0.2 parts by weight of known photosensitisers and of photosensitisers according to the invention are incorporated into unsaturated polyester resin according to the following formulation:

10.0 parts of unsaturated polyester resin (polyester based on maleic acid having a styrene content of 35%)
0.2 part of photosensitiser
0.1 part of a 10% solution of paraffin in toluene.

This mixture is stirred until the constituents are completely dissolved, and the solution subsequently applied, with a film-applier (500 mμ), to glass plates. The films are irradiated with a fluorescent lamp giving off a high proportion of UV-light, at a distance of 5 cm. After an exposure time of 20 minutes, the hardness of the films is determined by means of a pendulum apparatus (pendulum hardness according to König). The results of this series of tests are given in Table 3:

Table 3

| Sensitiser | Pendulum hardness according to Konig, after 20 min. irradiation |
|---|---|
| benzoin | 55 |
| benzoinisopropyl ether | 82 |
| benzildimethylacetal | 95 |
| benzildiethylacetal | 93 |
| benzildipropylacetal | 86 |
| benzildibutylacetal | 90 |
| benzil-di-β-methoxy-ethylacetal | 83 |

EXAMPLE 11

Determination of dark-storage stability

A 2% solution of known photosensitisers and of photosensitisers according to the invention in unsaturated polyester resin (polyester based on maleic acid having a styrene content of 35%) is prepared at 25°, and in each case the flow-through-time of a specific amount of the particular solution through a graduated buret determined. The solution is then stored in the dark at room temperature and, after 2, 4 and 8 weeks' storage time, the flow-through-time determined in the same manner. Polyester resin containing no additive is taken as a comparison. The results of these tests are given in Table 4:

Table 4

| Sensitiser | Flow-through-time in seconds | | | |
|---|---|---|---|---|
| | at start | after 2 weeks | 4 weeks | 8 weeks |
| polyester resin without additive | 275 | 265 | 283 | 278 |
| benzoin | 268 | 267 | 284 | 296 |
| benzoinisopropyl-ether | 272 | 278 | 281 | 283 |
| benzildimethyl-acetal | 265 | 270 | 280 | 280 |

The same mixtures were stored in the dark at 60° and the time before gelling occurred determined; the times are given in Table 5:

Table 5

| Sensitiser | Storage time at 60° before gelling occurs |
|---|---|
| benzoin | 70 h |
| benzoinisopropyl-ether | 190 h |
| benzildimethyl-acetal | >230 h |

EXAMPLE 12

Photocrosslinking of polyethylene

Benzildimethylacetal in a concentration of 0.5% is worked, on mixing rolls, into polyethylene of density 0.92. From the rolled sheet obtained are pressed films 0.1 mm in thickness, which are irradiated for 40 minutes with a high-pressure mercury vapour lamp at a distance of 10 cm. The irradiated film specimens are then extracted in boiling toluene for 5 hours. The extraction residue, which corresponds to the cross-linked proportion of the polyethylene, amounts to 24% of the weight of the film used. Without photosensitiser, but otherwise under the same conditions as those described above, no extraction residue remains.

EXAMPLE 13

Curing of printing pastes

A mixture of 70 parts of trimethylolpropane-trisacrylate,
10 parts of diallylphthalate-prepolymer and
20 parts of benzil-di-β-methoxyethyl-acetal, as bonding agent for inorganic and organic pigments, gels on being irradiated with a high-pressure mercury vapour lamp in less than 1 second.

The same result is obtained if, instead of methoxyethylacetal, the identical amount of benzil-dimethylacetal, benzil-dibutylacetal or benzil-di-β-bromoethylacetal is used.

We claim:

1. Process for the production of monoacetals of aromatic diketones of formula I $$Ar^1 - C = O \atop Ar^2 - C(OCH_2R^1)_2 \quad (I)$$

wherein $R^1$ represents hydrogen, alkyl having 1 to 5 carbon atoms, alkenyl having 2 or 3 carbon atoms, aralkyl having 7 to 9 carbon atoms, aralkenyl having 8 or 9 carbon atoms, or a group $-(CH_2)_n-X$, wherein n represents a whole number from 1 to 3, and X denotes halogen, $-OR^3$, $-SR^3$, $-OAr^3$, $-SAr^3$ $$-O-\overset{O}{\overset{\|}{C}}-R^3 \text{ or } -\overset{O}{\overset{\|}{C}}-OR^3$$

and $R^3$ represents alkyl having 1 to 4 carbon atoms, $Ar^1$, $Ar^2$ and $Ar^3$ each independently represent a phenyl radical unsubstituted, or at most trisubstituted by halogen, alkyl or alkoxy having 1 to 4 carbon atoms or by phenyl, which process comprises reacting an aromatic 1,2-diketone of the formula $Ar^1-CO-CO-Ar^2$ either with a sulphurous acid ester of the formula $(R^1CH_2O)_2SO$ in the presence of an anhydrous acid and a primary monoalcohol $R^1CH_2OH$ at a temperature of about 20° to 120° C. or with thionyl chloride and a primary monoalcohol $R^1CH_2OH$ at a temperature of from about 0° to 20° C. and subsequently heating to from about 20° to 120° C.

2. Process according to claim 1, wherein the anhydrous acid employed is concentrated sulphuric acid in an at least molar amount.

3. Process according to claim 1, wherein the aromatic 1,2-diketone is reacted with 3 to 4 moles of a sulphurous acid ester, or with at least 2 moles of thionyl chloride and at least 4 moles of a primary monoalcohol.

* * * * *

REEXAMINATION CERTIFICATE (681st)

United States Patent [19]

Brünisholz et al.

[11] B1 4,190,602

[45] Certificate Issued  May 19, 1987

[54] MONOACETALS OR AROMATIC 1,2-DIKETONES

[75] Inventors: Jean Brünisholz, Monthey; Rudolf Kirchmayr, Münchenstein, both of Switzerland

[73] Assignee: Ciba-Geigy Corporation, Ardsley, N.Y.

Reexamination Request:
  No. 90/000,496, Feb. 2, 1984
  No. 90/000,500, Feb. 13, 1984

Reexamination Certificate for:
  Patent No.: 4,190,602
  Issued: Feb. 26, 1980
  Appl. No.: 919,580
  Filed: Jun. 22, 1978

Related U.S. Application Data

[62] Division of Ser. No. 701,769, Jul. 2, 1976, abandoned, which is a division of Ser. No. 380,039, Jul. 17, 1973, abandoned.

[30] Foreign Application Priority Data

Jul. 28, 1972 [CH] Switzerland ............... 11295/72
Jun. 28, 1973 [CH] Switzerland ............... 9417/73

[51] Int. Cl.$^4$ ................................. C07C 45/00
[52] U.S. Cl. ........................... 568/315; 568/312; 568/314; 568/43; 568/42; 560/53; 560/255
[58] Field of Search .............. 568/312, 314, 315, 42, 568/43; 560/53, 255

[56] References Cited

U.S. PATENT DOCUMENTS

| | | | |
|---|---|---|---|
| 2,229,665 | 1/1941 | Mochel | 260/615 |
| 3,222,313 | 12/1965 | Horan et al. | 260/31.8 |
| 3,222,390 | 12/1965 | Horan et al. | 260/473 |
| 3,222,391 | 12/1965 | Horan | 260/473 |
| 3,715,293 | 2/1973 | Sandner et al. | 204/159.14 |

FOREIGN PATENT DOCUMENTS

1051269 of 1959 Fed. Rep. of Germany .

OTHER PUBLICATIONS

Organic Preparations, C. Weygand, 1945, p. 188: Interscience Publishers, Inc., New York.
Synthetic Organic Chemistry, R. B. Wagner and H. D. Zook, pp. 262 and 276, 1953: John Wiley and Sons, New York.
Patai, The Chemistry of Ether Linkages, pp. 317 and 318 (1967).
Organikum, VEB Deutscher Verlag d. Wissensch, pp. 486-488 (1976).
Voss/Annalen d. Chemie 485, 283-293 (1931).
Houben-Weyl, Methoden d. Organ. Chemie VII/1, 4-21-2 (1954).
Hesse, et al., Berichte 93, 1249-1251 (1960).
Kuhn, Trischmann, Chem. Berichte 94, 2258-2263 (1961).
Fieser and Fieser, Reagents for Organic Syntheses, vol. I, 683 and 1130 (1967).
Houben-Weyl, Methoden d. Organ. Chemie VI/2,439 (1963).
Fischer, Giebe, Berichte Deutschen Chem. Ges. 30,3054 (1897).
McElvain, Curry, J. Amer. Chem. Soc. 70, 3781-3786 (1948).
Harris, J. Chem. Soc. 2247 (1950).

*Primary Examiner*—James H. Reamer

[57] ABSTRACT

Monoacetals of aromatic diketones in which the acetal group is derived from primary mono- or dialkohols are useful as sensitizers in the photochemical polymerization or photochemical crosslinking of polymers. They are prepared from the diketones (benzils) by reaction with sulfites. The sulfites and the benzils may be formed immediately before the reaction in the same vessel without isolating these compounds. Most of the benzil monoacetals are new compounds.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-3 are cancelled.

* * * * *